United States Patent [19]
Casalnuovo et al.

[11] Patent Number: 5,382,697
[45] Date of Patent: Jan. 17, 1995

[54] PEEPARATION OF TRIARYLBORANE

[75] Inventors: Albert L. Casalnuovo; Thomas Foo, both of Wilmington, Del.

[73] Assignee: E. I. Du Pont de Nemours and Company, Wilmington, Del.

[21] Appl. No.: 264,275

[22] Filed: Jun. 23, 1994

[51] Int. Cl.$^6$ ................................................ C07E 9/02
[52] U.S. Cl. ............................................ 568/1; 568/6
[58] Field of Search ............................ 568/1, 6; 556/7

[56] References Cited

U.S. PATENT DOCUMENTS

| | | | |
|---|---|---|---|
| 3,798,256 | 3/1974 | King et al. | 260/465.8 |
| 4,082,811 | 4/1979 | Shook | 556/7 |
| 4,134,923 | 1/1979 | Reimer | 260/606.5 |
| 4,394,321 | 7/1983 | Cone | 556/7 |
| 4,416,824 | 11/1983 | Reimer et al. | 556/7 |
| 4,749,801 | 6/1988 | Beatty et al. | 556/7 |
| 4,847,399 | 7/1989 | Hollock et al. | 568/1 |

Primary Examiner—James H. Reamer

[57] ABSTRACT

Preparation of triarylborane from catalyst residues containing nickel complexes with triarylborane by heating the complexes at reduced pressure, and recovering the triarylborane by condensation.

4 Claims, 1 Drawing Sheet

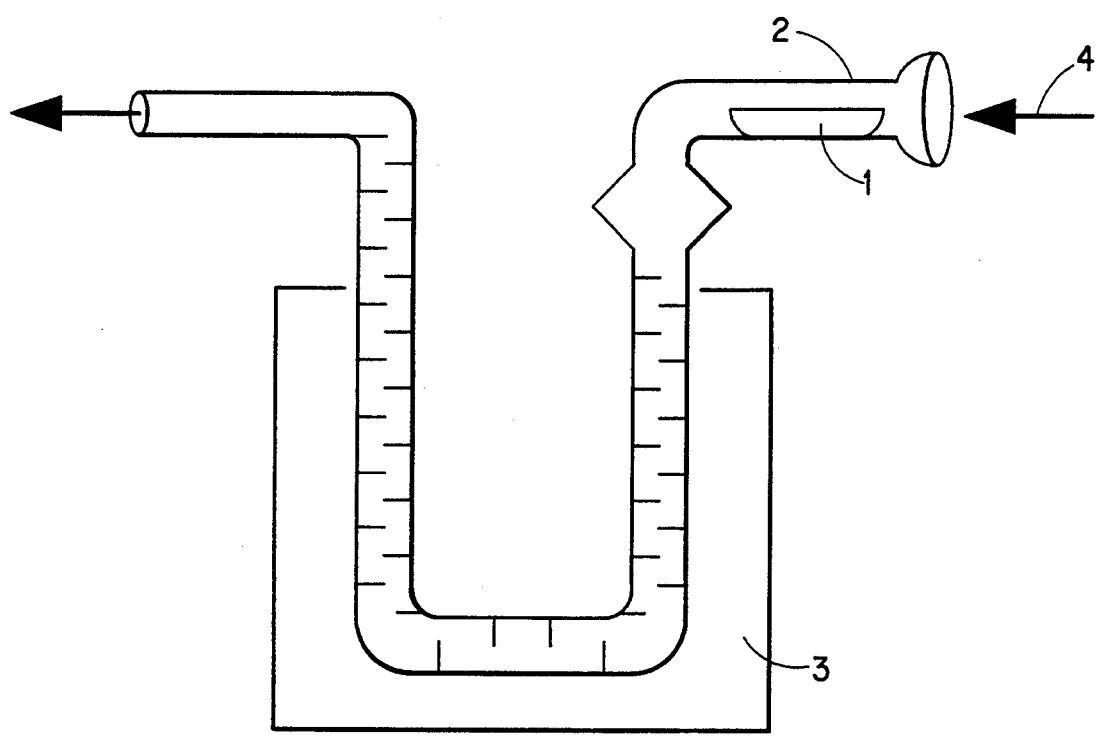
FIGURE

PREPARATION OF TRIARYLBORANE

FIELD OF THE INVENTION

This invention relates to the preparation of triarylborane from nickel complexes of the formula: $Ni(NC(CH_2)_4CN)_2(NCBAr_3)_2$ where Ar is phenyl or phenyl substituted with an alkyl group having 1 to 4 carbon atoms where the alkyl group may contain one or more fluorine atoms. These nickel complexes may be contained in catalytic residue formed during the alkene hydrocyanation (for example butadiene hydrocyanation) using organophosphorous nickel complexes as catalysts and triarylborane as catalytic promoters.

BACKGROUND OF THE INVENTION

King et al. U.S. Pat. No. 3,798,256 discloses the hydrocyanation of 3-pentenenitrile to produce adiponitrile using nickel complexes as catalysts and organic boron compounds as promoters. Such hydrocyanation reactions produce catalyst residues which are primarily $Ni(NCR)_4(NCBAr_3)_2$ hereinafter referred to as NCBCs. Shook U.S. Pat. No. 4,082,811 discloses treating such residues with ammonium hydroxide to precipitate the amine adduct of triarylborane. The triarylborane can be recovered from the adduct by treatment with metal hydroxide—see Shook U.S. Pat. No. 4,134,923.

The present invention is a direct method of recovery of the triarylborane promoter from the catalyst residue.

SUMMARY OF THE INVENTION

The present invention is a process for the manufacture of a triarylborane having the formula: $BAr_3$ where Ar is phenyl or phenyl substituted with an alkyl group having 1 to 4 carbon atoms where the alkyl group nay contain one or more fluorine atoms, which comprises heating a complex of the formula: $Ni(NC(CH_2)_4CN)_2(NCBAr_3)_2$ where Ar is as above, in an inert atmosphere at a pressure less than atmospheric to a temperature in the range of 120 degrees C to 300 degrees C; thus forming a vapor containing the triarylborane, and condensing triarylborane from the vapor. In a preferred embodiment of the process an inert gas stream moves the vapor containing triarylborane to a zone where the triarylborane is condensed.

DESCRIPTION OF THE DRAWING

The drawing is a diagrammatic cross-sectional view of an apparatus suitable for use in carrying out the process of the invention.

DETAILED DESCRIPTION OF THE INVENTION

In one embodiment of the invention, the catalyst residue or NCBC is placed in a conventional sublimation apparatus and then heated under an inert atmosphere such as nitrogen or argon, or, preferably, under reduced pressure to decompose the catalyst residue or NCBC and release $BAr_3$ and RCN. $BAr_3$ and RCN solidify on the sublimer cold finger. Temperatures ranging from 120° C. to 300° C. may be used, 170° C. to 230° C. is preferred. Pressures ranging from 0 to 760 torr may be used, 0.001 to 40 torr is preferred.

In a second embodiment of the invention, the catalyst residue or NCBC is placed in a tube and then heated, preferably under reduced pressure, while a stream of an inert carrier gas, such as nitrogen or argon, is passed over the catalyst residue or NCBC and through a cold trap. $BAr_3$ and RCN released during this process are swept into the trap by the carrier gas and condensed onto the surface of the trap.

The catalyst residue is obtained from alkene, preferably 3-pentenenitrile (3PN), hydrocyanations carried out in the presence of the active Ni catalyst $Ni[P(OR)_3]_4$ and a triarylborane promoter of the formula $BAr_3$, where R is an aryl radical having up to 18 carbon atoms and Ar is an aryl radical having up to 10 carbon atoms, preferably $BPh_3$ (Ph=phenyl). Typical Ni catalysts of this type include $Ni[P(OC_6H_5)_3]_4$, $Ni[P(O-p-C_6H_4CH_3)_3]_4$, $Ni[P(O-m-C_6H_4CH_3)_3]_4$, and $Ni[P(O-m\&p-C_6H_4CH_3)_3]_4$. The amount of promoter used can generally be varied from about 1:16 to 50:1 mole ratio of promoter to catalyst. A detailed description of the formation of catalyst residue is found in U.S. Pat. No. 4,082,811.

NCBC's can be prepared as described in Cone U.S. Pat. No. 4,394,321.

EXAMPLES

In the following examples, unless stated otherwise, all operations were carried out under a nitrogen atmosphere using a drybox or standard Schlenk techniques. Exposure of triphenylboron to air or moisture typically leads to the formation of diphenylboron derivatives. ADN-NCBC refers to the NCBC derived from adiponitrile (ADN), specifically $Ni(NC(CH_2)_4CN)_2(NCBPh_3)_2$. Elemental analyses for the catalyst residue and ADN-NCBC were as follows. Ni Catalyst residue: C, 72.96; H, 5.66; N, 10.53. ADN-NCBC: C, 72.14; H, 5.70; N, 11.71; Ni, 6.56; B, 4.26.

Example 1

0.158 g (0.195 mmol) of ADN-NCBC was placed in a sublimer equipped with a dry ice cold finger and then heated at 150° C. at 0.004 torr for 15 minutes, whereupon a white solid began to form on the cold finger. The temperature was increased to 190° C. for 30 minutes and then, finally, 200° C. for 4 hours. The apparatus was cooled to room temperature and the white solids collected from the cold finger. Yield 0.133 g. $^1H$ NMR spectroscopic analysis of these solids indicated a 1.5:1 mix of ADN to $BPh_3$, and a small amount of a diphenylboron derivative. Yield of $BPh_3=83\%$.

Example 2

2.0 g of Ni catalyst residue was heated to 210° C. at about 0.004 torr in a sublimer equipped with a dry ice cold finger. After 1 day the temperature was increased to about 230° C. for several hours. After cooling the apparatus to room temperature, 1.192 g of a white solid was collected from the cold finger and analyzed by $^1H$ NMR spectroscopy. The sample contained a mixture of $BPh_3$ and adiponitrile in a ratio of 1.0:1.1, and a small amount of a diphenylboron derivative. Yield of $BPh_3=71\%$.

Example 3

5.0 g of Ni catalyst residue was placed in a ceramic boat 1, inside a glass tube 2, as shown the figure. The pressure inside the system was reduced to about 20 torr while a nitrogen stream 4, was passed over the catalyst residue at a rate of about 200 ml/min. The tube was heated at 190° C. for about 5 hours and the volatile products collected in the dry ice trap 3. 3.4 g of a pale yellow solid was collected from the trap. $^1$H NMR spectroscopic analysis of the product indicated a mixture of BPh$_3$ and ADN that was 65% by weight BPh$_3$.

Hydrocyanation Performance Of BPh$_3$ Obtained from Degraded Catalyst.

Evaluation of the material containing triphenylboron recovered from degraded hydrocyanation catalyst in the manner described above for hydrocyanation activity was performed in a single-stage, 22-ml glass continuous stirred-tank reactor. U.S. Pat. No. 4,874,884, which is incorporated herein by reference, describes the use of continuous stirred-tank reactor to evaluate promoter performance. The steady-state conditions for the continuous hydrocyanation were as follows:

Reaction rate=1.0×10 E-4 moles ADN / liter-second
20% conversion of 3PN
0.1 moles of Ni(TTP)$_4$ catalyst/mole HCN fed (where TTP refers to tritolylphosphite) 0.12 moles of TTP/mole HCN fed
0.0065 moles of BPh$_3$/mole HCN fed
Temperature=40° C.

The reactor was initially charged with a 3PN solution containing 24 wt.% Ni(TTP)$_4$ catalyst, 6.3% TTP, and 0.28% BPh$_3$. The steady-state conditions were achieved by pumping the following solutions in a continuous fashion for 41 hours:

| Reagent | Feed Rate |
| --- | --- |
| 25 wt. % HCN in 3PN | 0.88 g/hr. |
| 2.24% BPh$_3$ in 3PN | 0.57 g/hr. |
| 35% TTP in 3PN | 0.66 g/hr. |
| 51% Ni(TTP)$_4$, 3.7% TTP in 3PN | 2.39 g/hr. |
| 3PN | 0.80 g/hr. |

The BPh$_3$ promoter solution was made with 52.0 g 3PN and 2.1 g of sublimed material, recovered from degraded Ni catalyst in the manner described in Example 2. Analysis of the solution by liquid chromatography showed that the solution contained 2.24 wt.% BPh$_3$.

The reactor product was collected from the reactor overflow for analysis by gas chromatography. The reaction of a given promoter can be characterized by the yields and selectivities shown below. The results shown are averaged over samples taken at 17 to 41 hours from the inception of continuous flow. As a comparison, the results are also shown for a continuous hydrocyanation under the same conditions, except for the use of BPh3 purchased on the commercial market as the promoter.

| | Recovered BPh$_3$ | Purchased BPh3 |
| --- | --- | --- |
| ADN Yield | 92.6% | 92.9% |
| Linearity | 96.2% | 96.3% |
| 2PN Yield | 3.7% | 3.6% |
| VN Yield | 0.04% | 0.04% |

Definitions:
Conversion=moles reacted/moles fed
VN=Valeronitrile
2PN=2-Pentenenitrile
MGN=Methylglutaronitrile
ESN=Ethylsuccinonitrile
ADN (2PN/VN) Yield=moles ADN (2PN/VN) produced moles 3PN reacted
Linearity=moles ADN/moles ADN+MGN+ESN.

What is claimed is:

1. A process for the manufacture of a triarylborane having the formula: BAr$_3$ where Ar is phenyl or phenyl substituted with an alkyl group having 1 to 4 carbon atoms where the alkyl group may be fluorinated, which comprises heating a complex of the formula: Ni(NC(CH$_2$)$_4$CN)$_2$(NCBAr$_3$)$_2$ where Ar is as previously defined, in an inert atmosphere at a pressure less than atmospheric to a temperature in the range of 120 degrees C. to 300 degrees C.; thus forming a vapor containing the triarylborane, and condensing triarylborane from the vapor.

2. The process of claim 1 in which an inert gas stream moves the vapor containing triarylborane to a zone where the triarylborane is condensed.

3. The process of claim 1 in which the complex is contained in catalyst residue.

4. The process of claim 1 in which Ar is phenyl.

* * * * *